United States Patent
Young

(10) Patent No.: US 7,618,405 B2
(45) Date of Patent: Nov. 17, 2009

(54) FLEXIBLE CONTAINER WITH A FLEXIBLE PORT AND METHOD FOR MAKING THE SAME

(75) Inventor: Harvey Theodore Young, Irvine, CA (US)

(73) Assignee: B. Braun Medical Inc., Bethlehem, PA (US)

( * ) Notice: Subject to any disclaimer, the term of this patent is extended or adjusted under 35 U.S.C. 154(b) by 11 days.

(21) Appl. No.: 12/025,282

(22) Filed: Feb. 4, 2008

(65) Prior Publication Data
US 2008/0140047 A1 Jun. 12, 2008

Related U.S. Application Data

(63) Continuation of application No. 10/660,815, filed on Sep. 12, 2003, now Pat. No. 7,354,426.

(51) Int. Cl.
*A61B 19/00* (2006.01)

(52) U.S. Cl. ............ 604/403; 604/408; 604/410; 604/411; 604/415; 604/6.16; 604/262; 383/78; 383/93; 383/94; 383/200; 383/202; 383/210; 383/38; 383/42; 383/59; 206/828; 206/461; 206/466; 220/62.11; 220/62.12; 220/660

(58) Field of Classification Search ........... 604/403, 604/408, 410, 411, 415, 6.16, 262; 206/828, 206/461, 466; 383/78, 93, 94, 200, 202, 383/210, 38, 42, 59; 220/62.11, 62.12, 660
See application file for complete search history.

(56) References Cited

U.S. PATENT DOCUMENTS 4,484,916 A 11/1984 McPhee
5,514,123 A 5/1996 Adolf et al.
5,681,627 A 10/1997 Mueller
5,976,300 A 11/1999 Buchanan et al.
6,127,009 A 10/2000 Strassmann
6,280,431 B1 * 8/2001 Domkowski et al. ........ 604/411
6,319,243 B1 11/2001 Becker et al.

(Continued)

FOREIGN PATENT DOCUMENTS

DE  202 14 638 U1  1/2003

OTHER PUBLICATIONS

International Search Report dated May 11, 2004 from related International Application No. PCT/US2003/31013, filed Sep. 23, 2003.

(Continued)

*Primary Examiner*—Tatyana Zalukaeva
*Assistant Examiner*—Ginger T Chapman
(74) *Attorney, Agent, or Firm*—Klein, O'Neill & Singh, LLP

(57) ABSTRACT

A flexible container incorporating flexible front and rear sheets and one or more container ports disposed in between the sheets are discussed. The one or more container ports each has a pliable attachment flange and an integrally molded nozzle. The pliable attachment flange has a first configuration whereby the attachment flange collapses to enable heat sealing the attachment flange to the sheets and thereafter substantially recovers its shape to provide a fluid pathway with the port. Various terminal ports, terminal caps, and rubber septums may be useable with the one or more container ports.

33 Claims, 11 Drawing Sheets

U.S. PATENT DOCUMENTS

| | | | |
|---|---|---|---|
| 6,394,993 | B1 | 5/2002 | Chang et al. |
| 6,726,667 | B2 | 4/2004 | Leise et al. |
| 6,726,672 | B1 * | 4/2004 | Hanly et al. ............... 604/414 |
| 6,846,305 | B2 * | 1/2005 | Smith et al. ............... 604/410 |
| 6,974,447 | B2 * | 12/2005 | Smith et al. ............... 604/415 |
| 2003/0060796 | A1 | 3/2003 | Andersson et al. |
| 2004/0049837 | A1 | 3/2004 | Falconer et al. |
| 2006/0276769 | A1 | 12/2006 | Domkowski et al. |

OTHER PUBLICATIONS

Response to 312 Amendment mailed Mar. 4, 2008 from related U.S. Appl. No. 10/660,815.

Notice of Allowance mailed Dec. 11, 2009 from related U.S. Appl. No. 10/660,815.

Office Action mailed Jun. 14, 2007 from related U.S. Appl. No. 10/660,815.

Office Action mailed Feb. 28, 2007 from related U.S. Appl. No. 10/660,815.

Office Action mailed Jul. 5, 2006 from related U.S. Appl. No. 10/660,815.

Office Action mailed Mar. 15, 2006 from related U.S. Appl. No. 10/660,815.

* cited by examiner

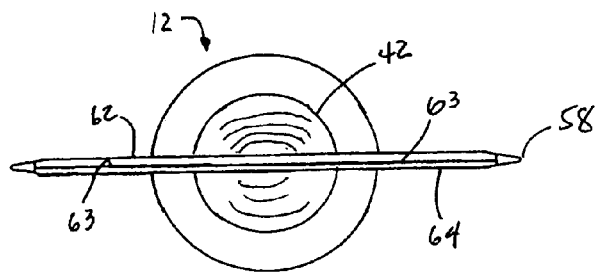
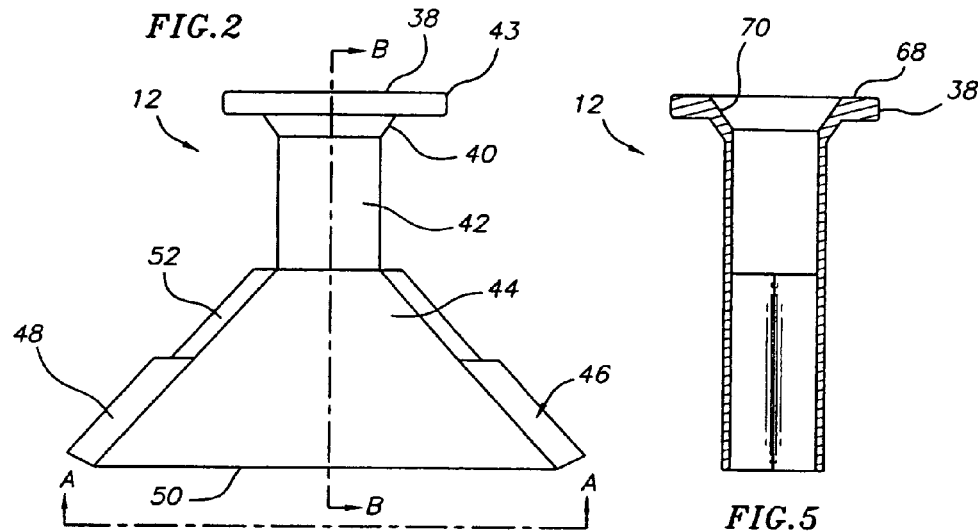
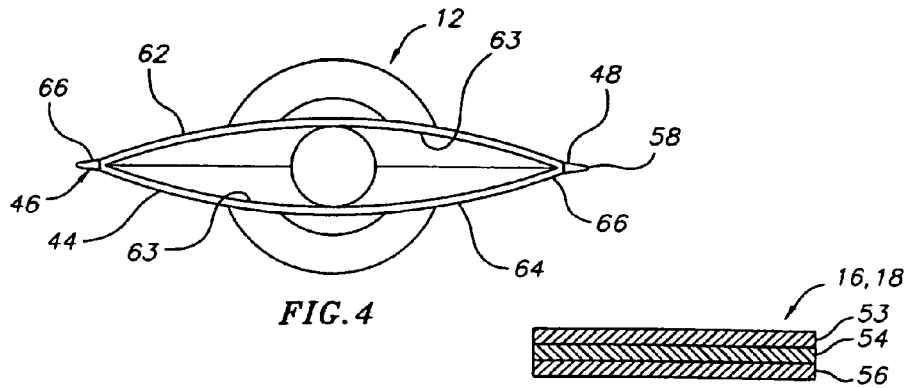

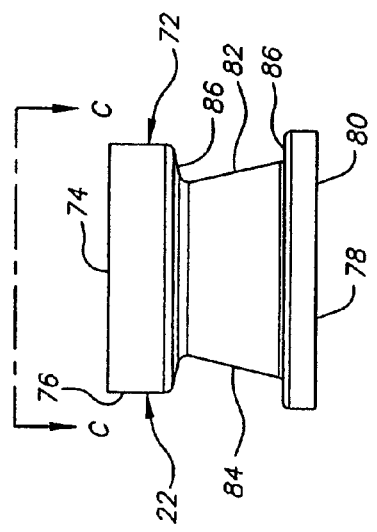
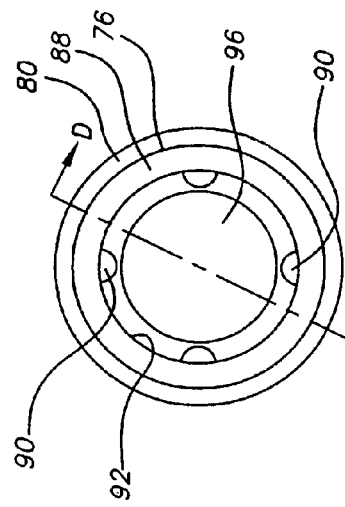
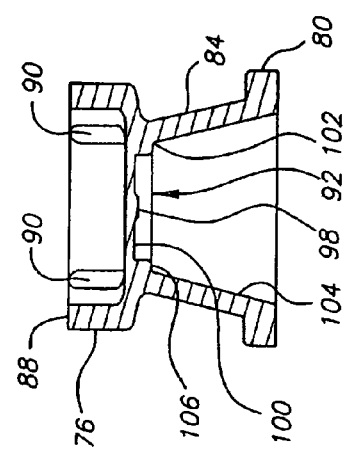
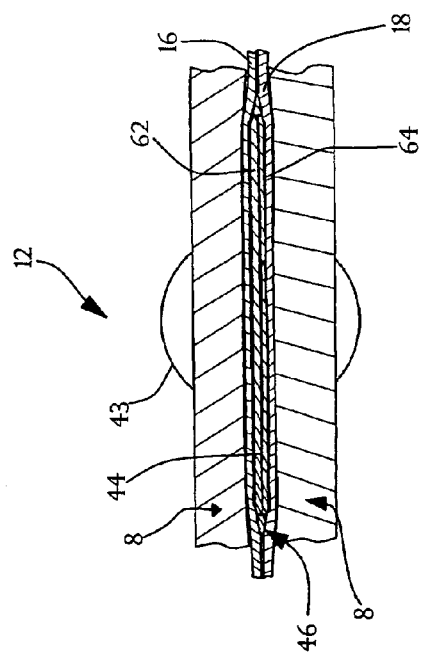
FIG. 6
FIG. 7
FIG. 8
FIG. 4B

FLEXIBLE CONTAINER WITH A FLEXIBLE PORT AND METHOD FOR MAKING THE SAME

CROSS-REFERENCED TO RELATED APPLICATION(S)

This is a Continuation application of Ser. No. 10/660,815, filed Sep. 12, 2003, now U.S. Pat. No. 7,354,426 the entire contents of which are expressly incorporated herein by reference as if set forth in full.

BACKGROUND

Flexible containers having a flexible front sheet sealed along a perimeter to a flexible rear sheet are generally discussed herein with particular discussions to flexible containers having a container port affixed in between the front sheet and rear sheet comprising a pliable attachment flange.

Flexible containers are widely used for packaging nutritional fluids, diluents, medicaments, IV solutions, and the like. Broadly speaking, these flexible containers are manufactured by affixing a first flexible sheet to a second flexible sheet along a perimeter and interposing one or more ports in between the two sheets for filling, for draining, and/or for supplementing or adding other fluids to the container. The sheets used to make the flexible containers may be made from single-layer flexible thermoplastic sheets or from multiple-layers flexible thermoplastic sheets. The one or more ports generally include a set port for access with the spike of a fluid administration set or an additive port for use with a needle. The flexible container may include peelable seals to form a multi-compartment containers.

A common characteristic among the prior art ports used with the prior art flexible containers is ports having a solid or non-pliable attachment flange with a contoured configuration. To heat seal these prior art attachment flanges to the front and rear sheets to thereby form the prior art flexible containers, contoured heat dies with matching contour configuration as the attachment flanges are used. The contoured heat dies heat and fuse the attachment flanges to the sheets to form flexible containers. Occasionally misalignment between the contoured heat dies and the contoured attachment flanges will occur thus resulting in inaccurate heat sealing of the ports to the sheets. As readily apparent, inaccurate heat seals will result in reject containers. In addition, by necessarily aligning the heat dies with the attachment flanges, production is negatively impacted due to the alignment requirement.

Accordingly, there is a need for a container comprising an easy to install port not highly dependent on alignment requirements.

SUMMARY

The present invention specifically addresses and alleviates the above-mentioned deficiencies associated with the prior art assemblies. More particularly, the present invention may be implemented by providing a flexible container comprising a flexible front sheet and a flexible rear sheet attached to one another along at least one edge, a container port comprising a nozzle integrally molded to an attachment flange disposed in between the flexible front and rear sheets; wherein the attachment flange comprises: a first attachment flange layer comprising an interior surface and an exterior surface and a second attachment flange layer comprising an interior surface and an exterior surface attached to one another along at least one edge, a first configuration comprising the two interior surfaces of the first and second attachment flange layers contacting one another, at least in part, when positioned in between the flexible front and rear sheets and heat sealed to the flexible front and rear sheets with at least one heat bar, and a second configuration comprising the two interior surfaces spaced apart from one another at a location away from the at least one edge when the at least one heat bar is removed.

In another aspect of the present invention, there is provided a flexible container comprising: a flexible front sheet and a flexible rear sheet attached to one another along at least a portion of a common perimeter; a container port comprising a nozzle integrally molded to a flexible attachment flange attached to the flexible front and rear sheets; wherein the flexible flange comprises a first flange layer comprising an interior surface and an exterior surface attached to a second flange layer comprising an interior surface and an exterior surface; the two flange layers defining an interior cavity comprising a first opening and a larger second opening in fluid communication with the nozzle; and wherein at least a portion of the interior surface of the first flange layer contacts at least a portion of the interior surface of the second flange layer when the flexible attachment flange is compressed between the flexible front sheet and flexible rear sheet with a heat bar.

In still yet another aspect of the present invention, there is provided a flexible container comprising: a flexible front sheet and a flexible rear sheet attached to one another along a common perimeter; a container port comprising a nozzle integrally molded to a flexible attachment flange attached to the flexible front sheet and flexible rear sheet; the flexible attachment flange comprising a flexible front flange sheet attached to a flexible rear flange sheet along two common edges; a fin extending from each of the two common edges of the flexible attachment flange comprising a first thickness that tapers as it extends away from the common edge to a second thickness; a flexible front flange layer interior surface that temporary contacts, at least in part, a flexible rear flange layer interior surface as the flexible attachment flange is attached to the flexible front sheet and flexible rear sheet by a heat bar.

Yet, in accordance with another aspect of the present invention, there is provided a flexible container comprising a flexible front sheet and a flexible rear sheet attached to one another along a common perimeter; a container port comprising a nozzle integrally molded to a flexible attachment flange attached to the flexible front sheet and flexible rear sheet; the flexible attachment flange comprising a flexible front flange sheet attached to a flexible rear flange sheet along two common edges; a flexible front flange layer interior surface that temporary contacts, at least in part, a flexible rear flange layer interior surface as the flexible attachment flange is attached to the flexible front sheet and flexible rear sheet by a heat bar; and a terminal port comprising a punctureable membrane disposed in an interior cavity thereof, said terminal port being affixed to the container port.

BRIEF DESCRIPTION OF THE DRAWINGS

These and other features and advantages of the present invention will become appreciated as the same become better understood with reference to the specification, claims and appended drawings wherein:

FIG. 2 is a semi-schematic side view of a container port comprising a flexible attachment flange and usable with the container of FIG. 1 provided in accordance with aspects of the present invention;

FIG. 3 is a partial cross-sectional side view of a multi-layer flexible container sheet provided in accordance with aspects of the present invention;

FIG. 4 is a semi-schematic end view of the container port of FIG. 2 taken along line A-A;

FIG. 4B is a semi-schematic partial cross-sectional view of a pair of heat bars placed over the attachment flange of FIG. 4A, which is disposed in between an upper container sheet and a lower container sheet;

FIG. 4A is a semi-schematic end view of the container port of FIG. 4 with the attachment flange in a flattened state;

FIG. 5 is a semi-schematic cross-sectional side view of the port of FIG. 2 taken along line B-B;

FIG. 6 is a semi-schematic side view of a terminal port usable with the container port of FIG. 2 provided in accordance with aspects of the present invention;

FIG. 7 is a semi-schematic end view of the terminal port of FIG. 6 taken along line C-C;

FIG. 8 is a semi-schematic cross-sectional side view of the port of FIG. 7 taken along line D-D;

DETAILED DESCRIPTION

The detailed description set forth below in connection with the appended drawings is intended as a description of the presently preferred embodiments of flexible containers with flexible ports provided in accordance with practice of the present invention and is not intended to represent the only forms in which the present invention may be constructed or utilized. The description sets forth the features and the steps for constructing and using the flexible containers of the present invention in connection with the illustrated embodiments. It is to be understood, however, that the same or equivalent functions and structures may be accomplished by different embodiments that are also intended to be encompassed within the spirit and scope of the invention. Also, as denoted elsewhere herein, like element numbers are intended to indicate like or similar elements or features.

Figure 1:
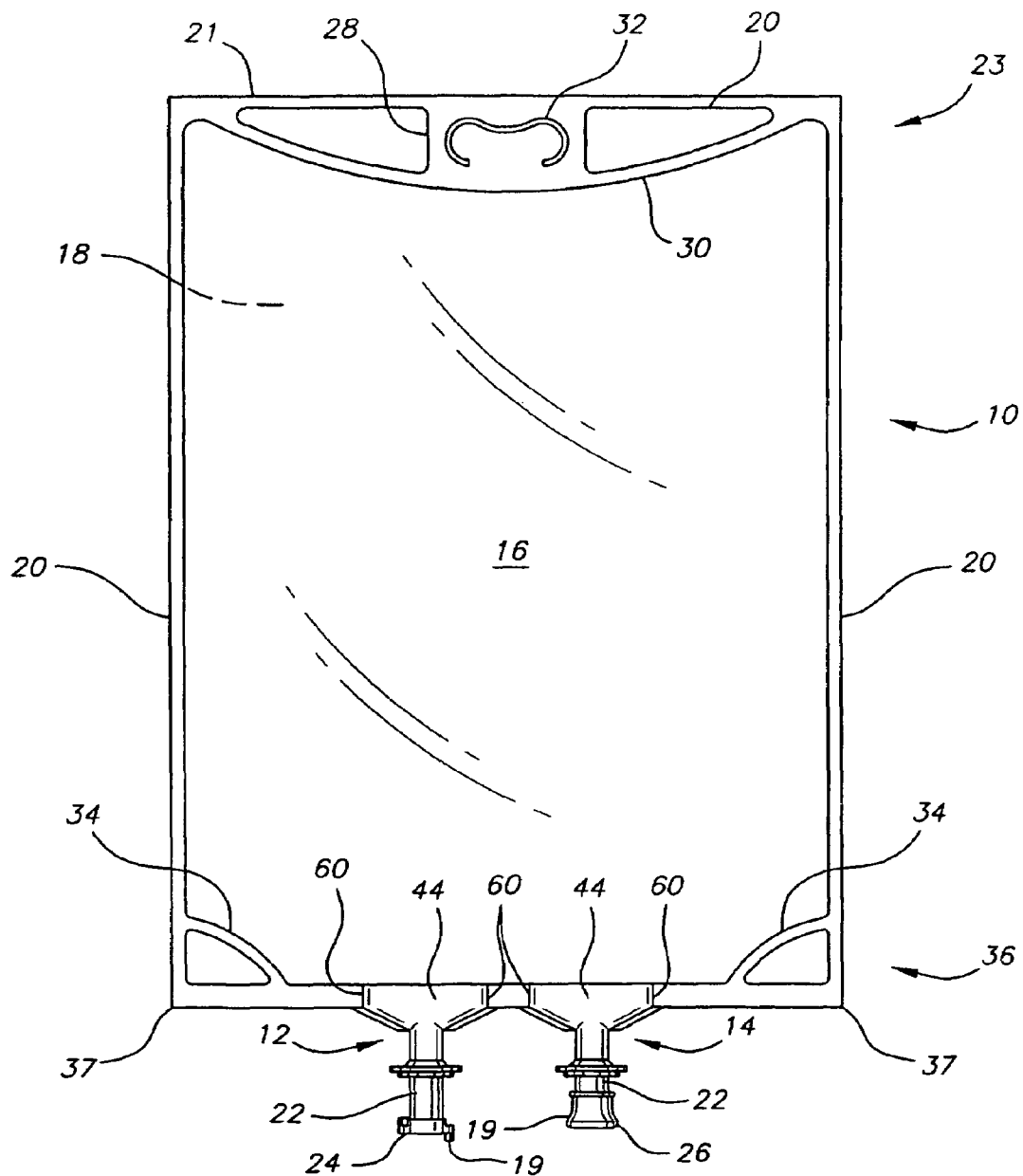
FIG. 1 is a semi-schematic side view of a container provided in accordance with aspects of the present invention.

Referring now to FIG. 1, there is shown an exemplary flexible container 10 provided in accordance with aspects of the present invention. The flexible container 10 comprises a first port 12 and a second port 14 sealed in between a first sheet 16 and a second sheet 18 (interposed subjacent the first sheet) via a perimeter seal 20. The first and second ports 10, 12 may function as a fill port, a drain port, or an additive port. The perimeter seal 20 defines a volumetric enclosure that varies in capacity depending on, among other things, the size of the first and second sheets 16, 18 and generally comprises a seal width of about 2-6 mm with 3 mm being more preferred. Exemplary volumes defined by the first and second sheets 16, 18 include about 100 ml to about 3000 ml with other volumes contemplated. The container may also incorporate variable volumes by utilizing stretchable first and second sheets that can stretch from a first surface area to a second larger surface area to thereby create a larger volumetric capacity. Exemplary stretchable containers are disclosed in U.S. Pat. No. 5,910,138, its content is expressly incorporated herein by reference.

Terminal devices for capping the ports 12, 14 are shown, which includes terminal ports 22 capped by selectable terminal caps 19. While additional terminal caps 19 are discussed further below, a set port cap 24 and an additive port cap 26 are shown capped to the terminal ports 22, which are attached to the first port 12 and second port 14, respectively. In one exemplary embodiment, the container 10 is constructed in accordance with aspects of the invention disclosed in U.S. Pat. No. 4,803,102 to Raniere et al., the content of which is expressly incorporated herein by reference.

The container 10 may incorporate one or more than two ports attached along one or more edges of the container 10 and, instead of two separate sheets, may be made by folding a single sheet and sealing the overlapping edges of the perimeter of the single sheet to form the container. Alternatively, the container 10 may be made with multiple compartments similar to those containers disclosed in U.S. Pat. Nos. 5,910,138; 5,928,213, 5,944,709; 6,165,161; and 6,203,535, their contents are expressly incorporated herein by reference. Moreover, the multiple compartments can be divided such that the contents are mixed prior to exiting one or more drain ports as an admixture or alternatively be divided such that each stored component is separately in fluid communication with a fill/drain port.

Optionally, a hanging flap 28 may be incorporated in between the top perimeter seal 21 and an inner perimeter seal 30 near the top end 23 of the container. In one exemplary embodiment, the inner perimeter seal 30 comprises an arcuate seal comprising a bending radius of about 100 to about 300 millimeters and can vary with the size of the container. The hanging flap 28 includes one or two overlapping hanging holes 32 for hanging the container 10 on a pin or a hook. The hanging holes may also be a frangible or a weaken section of the hanging flap 28 for subsequent removal by a user. In another exemplary embodiment, the hanging flap 28 may be separated from the top perimeter seal 21 such that the flap pivots or anchors from the arcuate inner perimeter seal 30.

One or more drain seals 34 may be incorporated along the bottom end 36 of the container 10. The drain seals may comprise a pair of generally arcuate heat seals 34 formed at the corners 37 of the lower end 36 of the container. The drain seals 34 facilitate or direct fluids stored inside the container to flow toward the first and second ports 12, 14 for draining out from at least one of the ports. In one exemplary embodiment, the drain seals comprise a bending radius of about 20 to about 150 millimeters. However, depending on the size of the container, other bending radii may be incorporated.

Turning now to FIG. 2, a semi-schematic side view of a port provided in accordance with aspects of the present invention is shown, which may be the first port 12 or the second port 14 shown in FIG. 1. For ease of reference, only port 12 is discussed although it is understood that the same disclosure applies to port 14.

The port 12, or sometime alternatively referred to as a container port, comprises a flange 38, a tapered or reduced neck 40, a generally cylindrical nozzle 42, an attachment flange 44, which resembles a diffuser or funnel, and a plurality of fins or ribs 46. The cylindrical nozzle 42 is in fluid communication with the cavity defined by the attachment flange 44, which has a first flange opening near the base 50 and a relatively smaller second opening at the interface with the nozzle 42. The fins or ribs 46 each comprises a first fin section 48 near the base 50 of the attachment flange 44 and a second smaller fin section 52 nearer the interface between the nozzle 42 and the attachment flange 44. Alternatively, the first and second fin sections 48, 52 can mesh or have a uniform shape such that no line of demarcation exists between the two fins. An optional protrusion 43 is formed radially on a perimeter portion of the flange 38 and extends radially about 1 mm to about 2.5 mm with 1.3 mm being preferred. The protrusion 43, when incorporated, facilitates injection of molten plastic during the molding process.

In one exemplary embodiment, the container port 12 is integrally molded from a blend of polypropylene-ethylene random copolymer and styrene ethylene-butylene styrene thermoplastic elastomer (SEBS) in a wt-wt ratio of about 95:5 to about 30:70. In one preferred embodiment, a ratio of 80:20 wt-wt ratio of polypropylene-ethylene random copolymer to SEBS is blended to form the port 12 of the present exemplary embodiment. The SEBS is commercially available from KRATON Polymers Company under the trade name KRATON having a commercial designation G1652. The polypropylene-polyethylene copolymer is available from Atofina Petrochemicals Company of Houston, Tex., having a commercial designation of Z9450. In practice, the blend is made by mixing pellets of the Z9450 co-polymer resin and G1652 thermoplastic elastomer, in crumb form, in a 80:20 wt-wt ratio, or some other desired ratio depending on the desired finished product, in a high shear mixer and melting and repelletizing the mixture. Subsequently, the port 12 is formed from the blended pellets in a commercial injection molding process. The formed port 12 has a semi-rigid consistency that allows the attachment flange to collapse when heat sealed to the first and second sheets 16, 18 using flat heat bars yet resilient enough to recover most if not all its structure subsequent to the heat sealing process, as further discussed below.

Referring again to FIG. 1, the attachment flanges 44 of the container ports 12, 14 may be secured to the first and second sheets 16, 18 and more particularly to the interior surfaces of the first and second sheets. In one exemplary embodiment, the first and second sheets 16, 18 are made from multiple layer films comprising materials that are compatible with the port material. Referring to FIG. 3, a multi-layer film is shown. The multiple layer film 16 or 18 may comprise an outer layer 53, a middle layer 54, and an inner layer 56. As disclosed in U.S. Pat. No. 4,803,102, which has previously been incorporated, the composition of the inner layer 56 comprises a polypropylene-polyethylene copolymer and SEBS, similar to the composition of the container ports 12, 14.

The outer layer 53 may comprise either polyether block amide copolymer (PEBA) or an abuse resistant material containing ester groups, referred to as EGM's. One exemplary EGM is a copolyester available from Eastman Kodak Company of Rochester, N.Y., under the product name Eastman PCCE 9967. PCCE 9967 is a glycol modified cyclohexanedimethano-cyclohexane-dicarboxylate. The outer layer 53 can also contain polycarbonate (PC). The middle layer 54 may vary depending on whether the outer layer 53 is made from a blend of EGM or PEBA. Where the outer layer 53 is an EGM, particularly favorable material for use as the middle layer 54 is SEBS. Where the outer layer 53 is made from a blend of PEBA, suitable materials for use as the middle layer 54 are carboxy modified polypropylenes such as Admer QF-500, QF-550, and QF-551, which are commercially available from Mitsui Petrochemical.

Overall, the film thickness of the multi-layer films 16, 18 can range from about 1.5 mils to about 20 mils, with a preferred range of about 6 mils to about 12 mils. Within this preferred family of films, preferred ratios of the layers to the overall thickness of the three layer composite are about 60% to about 85% inner layer 56, about 5% to about 30% outer layer 53, and about 7% to about 15% middle layer 54. A more preferred film is about 77% layer 56 as a blend of PPE and SEBS, about 13% layer 53 as copolyester, and about 10% layer 54 as SEBS.

The container 10 of FIG. 1 may be made by first forming the perimeter seals 20, the drain seals 34, the inner perimeter seal 30, and the hanging flap 28, except for the perimeter seal at the edge of the bottom end 36. The container is preferably made by placing the inner layer 56 (FIG. 3) of the first and second sheets 16, 18 in opposing configuration and then applying one or more appropriate heat bars at a temperature of about 250° F. or higher at a pressure of about 90 psi, and for at least 3 seconds or more. The attachment flanges 44 of the ports 12, 14 are inserted in between the inner layers 56 of the first and second sheets 16, 18 and then a sufficiently long flat heat bar or bars are used to fuse the attachment flanges to the sheets. Alternatively, the attachment flange 44 from each of the ports may be fused separately or sequentially to the sheets instead of attaching them at the same time.

In one exemplary embodiment, heat bars with coated vulcanized rubber are used to fuse the attachment flanges 44 of the container ports 12, 14 to the first and second sheets 16, 18. The heat bars with vulcanized rubber are commercially available from United Silicone, Lancaster, N.Y. The vulcanized rubber is a Silicone Rubber Compound.

Referring now to FIG. 4, a semi-schematic bottom view of the port 12 of FIG. 2 is shown, taken at line A-A. Assuming that the port 12 is placed in between two sheets and fused by flat heat bars, in this fused configuration, the tip 58 of the first fin section 48 of each fin 46 and the sheets 16, 18 define two channels, one on each of the two sides of each fin. Preferably, each channel is sealed or fused (i.e., have no gap or hole) when the attachment flanges are sealed to the first and second sheets so that liquid contained within the container 10 cannot leak through the channels 60 (FIG. 1). To facilitate such fusion, in one exemplary embodiment, the port 12 is implemented with a configuration that facilitates bonding with the sheets 16, 18.

Still referring to FIG. 4, the attachment flange 44 comprises an oblong structure comprising a first attachment flange layer 62 joined to a second attachment flange layer 64 along their respective edges 66. In one exemplary embodiment, the edges 66 are creases formed when the angled sides of the flange layers 62, 64 are molded together. The first and second attachment flange layers 62, 64 have a wall thickness of about 0.4 to about 1.5 millimeters with 0.7 millimeter being more preferred. The length of the attachment flange measured from one attachment flange edge 66 to the other attachment flange edge 66 is about 29.5 mm with about 15 mm to about 50 mm being a usable range. The first fins 48 each comprises a fin width of about 6 mm and has about a 10 to about a 30 degree draft angle or taper that terminate into a round tip with a 20 degree angle being more preferred. The fin has a thickness of about 1.30 mm measured at its widest point with larger or smaller fins being acceptable. The first and second attachment flange layers 62, 64 also each comprises an interior surface 63 that touches one another, at least along a portion of the base section 50 of the attachment flange, when the attachment flange is placed in between the first and second sheets and sealed thereto by flat heat bars. This is shown in FIG. 4A with the flat heat bars omitted for clarity. Subsequent to removing the flat heat bars, the first and second attachment flange layers recover their shape or configuration as shown in FIG. 4 with the interior surface of each respective flange layer in a spaced apart relationship relative to one another, except at the edges where they combine. This recovery is aided, at least in part, by the arcuate surface of the flange layers 62, 64.

Among the advantages of the container provided in accordance with aspects of the present invention, gas purging is simplified by the flexible attachment flange 44. As is known to a person of ordinary skill in the art, some solutions to be packaged in the flexible container 10 may be sensitive to oxygen or other atmospheric gases. Thus, these solutions normally have to be filled in a controlled environment. Among the steps required for handling solutions sensitive to oxygen or other atmospheric gases, a container for storing such a sensitive solution normally requires flushing or purging with an inert gas, such as with a nitrogen gas. The purged container is then clamped shut near the container port and attached to a filling system for filling the container with the sensitive solution. The clamp is removed subsequent to placing the flattened container in communication with a filling port of the filling system. Following the filling step, the container is again clamped near the container port before being transferred to a welding station for welding on a terminal port. Subsequent to the welding step, the clamp is removed.

FIG. 4B is a semi-schematic partial cross-sectional side view of the attachment flange 44, which comprises flange layers 62, 64, placed between a first sheet 16 and a second sheet 18. The stacked layers are then placed between a pair of heat bars 8, which compress the two flange layers 62, 64, together. The heat bars 8 fuse the attachment flange 44 to the two container sheets 16, 18 and upon removing the two heat bars, the attachment flange 44 reverts to, or close to, its normal configuration shown in FIG. 4.

The pliable attachment flange 44 provided in accordance with aspects of the present invention facilitates the filling process with solutions sensitive to oxygen or other atmospheric gases. Among other things, because the pliable attachment flange can be pinched flat, less residual gas remains in the container before the container is filled with the oxygen or other gas sensitive solution. This is also true when the filling nozzle 12 or 14 is removed from the filling port following the filling step to permit attachment of the terminal end 22 to the container nozzle. The ability to easily close the filling port by pinching the attachment flange flat also enhances the control of ullage of the container.

FIG. 5 is a semi-schematic cross-sectional side view of the port 12 of FIG. 2 taken along line B-B. In one exemplary embodiment, the port 12 has about a 6.6 mm ID and a wall thickness of about 1.0 mm. The flange 38 has a diameter of about 17 mm, a flange thickness of about 2 mm, and comprises a raised face 68 comprising a raised thickness of about 0.5 mm and a diameter of about 14.5 mm. The inside tapered surface 70 comprises about a 25 to about a 50 degree angle from vertical with about 39 degrees being more preferred. In one exemplary embodiment, the diameter of the port and the length of the port are selected for implementation and then the tapered angle selected to compliment the selected length and diameter. Other dimensions may be implemented without deviating from the scope of the present invention, which may depend on the designer's choice, container size, particular terminal port, particular terminal cap selected, and IV administration set to be used.

FIG. 6 is a semi-schematic side view of a terminal port 22 provided in accordance with aspects of the prevent invention, which may be referred to as an additive port 72. The additive port 72 has a first end 74, which comprises a straight terminal end comprising a generally cylindrical port section 76, and a second end 78, which comprises a mating flange 80. The additive port 72 is useable with the container port 12 of FIG. 2 by affixing, such as by heat-sealing, the second end 78 to the flange 38 of the container port 12 via conventional means, such as by a radiant heat process, by heat sealing, by impulse sealing, by ultrasonic welding, by hi-frequency induction heating, or by hot plate welding.

An intermediate section 82 comprising a tapered portion 84 connects the first end 74 with the second end 78. At the two intersections 86 where the tapered portion 84 meets the first end 74 and the second end 78, curved transitions are preferred, which may instead comprise square intersections or curved transitions comprising different curves. In one exemplary embodiment, the additive port 72 is made from the same material composition as the container port 12, with variations in the composition range as discussed above for the container port 12 and container sheets being acceptable. In an alternative embodiment, the material makeup of the additive port 72, i.e., the percent composition of each component, is preferably selected to include a higher durometer or hardness than the container port 12. When incorporated, the higher durometer enhances attachment of the aluminum closure. In one exemplary embodiment, the first end 74 of the additive port 72 comprises an outside diameter of about 13 mm, the second end 78 comprises an outside diameter of about 15 mm, and the length of the additive port 72 measured from the first end to the second end is about 11 mm. However, depending on the service, intended use, terminal caps, geographic destination of use, etc., the sizes may vary without deviating from the spirit and scope of the present invention.

Referring now to FIG. 7, an end view of FIG. 6 taken at line C-C is shown. In the FIG. 7 plan view, a portion of the mating flange 80 is shown along with the cylindrical end 88 of the generally cylindrical port section 76, a plurality of ribs 90, and a central puncture-able seal or membrane 92. The ribs 90 extend radially inwardly from the interior surface 94 of the cylindrical port section 76, which defines a receiving chamber 96, and reduce the effective inside diameter of the cylindrical port section by a corresponding amount as the thickness of the ribs. Although four ribs 90 are shown, fewer or more ribs may be implemented without deviating from the scope of the present invention.

A rubber septum may be placed in the receiving chamber 96 of the port. Once placed, the rubber septum is centered by the ribs in the terminal end of the port. An aluminum crimp (FIG. 16) compresses the flange of the rubber septum to provide a seal. In this compressed configuration, the bottom of the rubber septum is compressed against the surface of the central puncture-able seal 92 to provide a seal. In one exemplary embodiment, the outside diameter of the cylindrical port section 76 is about 13 mm and the inside diameter is about 10 mm. The ribs 90 each extend radially inwardly approximately 1 mm. The rubber septum is commercially available from a number of manufacturers including West Pharmaceutical Services, Lionville, Pa.

FIG. 8 is a cross-sectional side view of the additive port 72 of FIG. 7 taken along line D-D. As shown, the ribs 90 extend roughly the height of the receiving chamber 96. Alternatively, the ribs may be eliminated by selecting a septum with a larger diameter than the inside diameter of the port to allow the interior surface of the port to center the rubber septum. The central puncture-able seal 92 is integrally molded with the port 72 and comprises a non-uniform seal layer thickness, with uniformity being an acceptable option. In one exemplary embodiment, the central puncture-able seal 92 comprises a raised central portion 98 comprising a thickness of about 0.7 mm and a shallow perimeter portion 100 comprising a thickness of about 0.3 mm. The raised portion 98 and the central portion 100 are incorporated to facilitate injection molding. In an alternative embodiment, the raise central portion 98 comprises a raised or dome surface extending from the perimeter portion 100, rather than a solid build-up portion as shown in FIG. 8. Still alternatively, the interior cavity defined by the generally cylindrical portion section 76 may comprise a flared section near the cylinder end 88 and may comprise indentations and protrusions for accommodating rubber septums having non-uniform surfaces or that require special mating surfaces.

Figure 16:
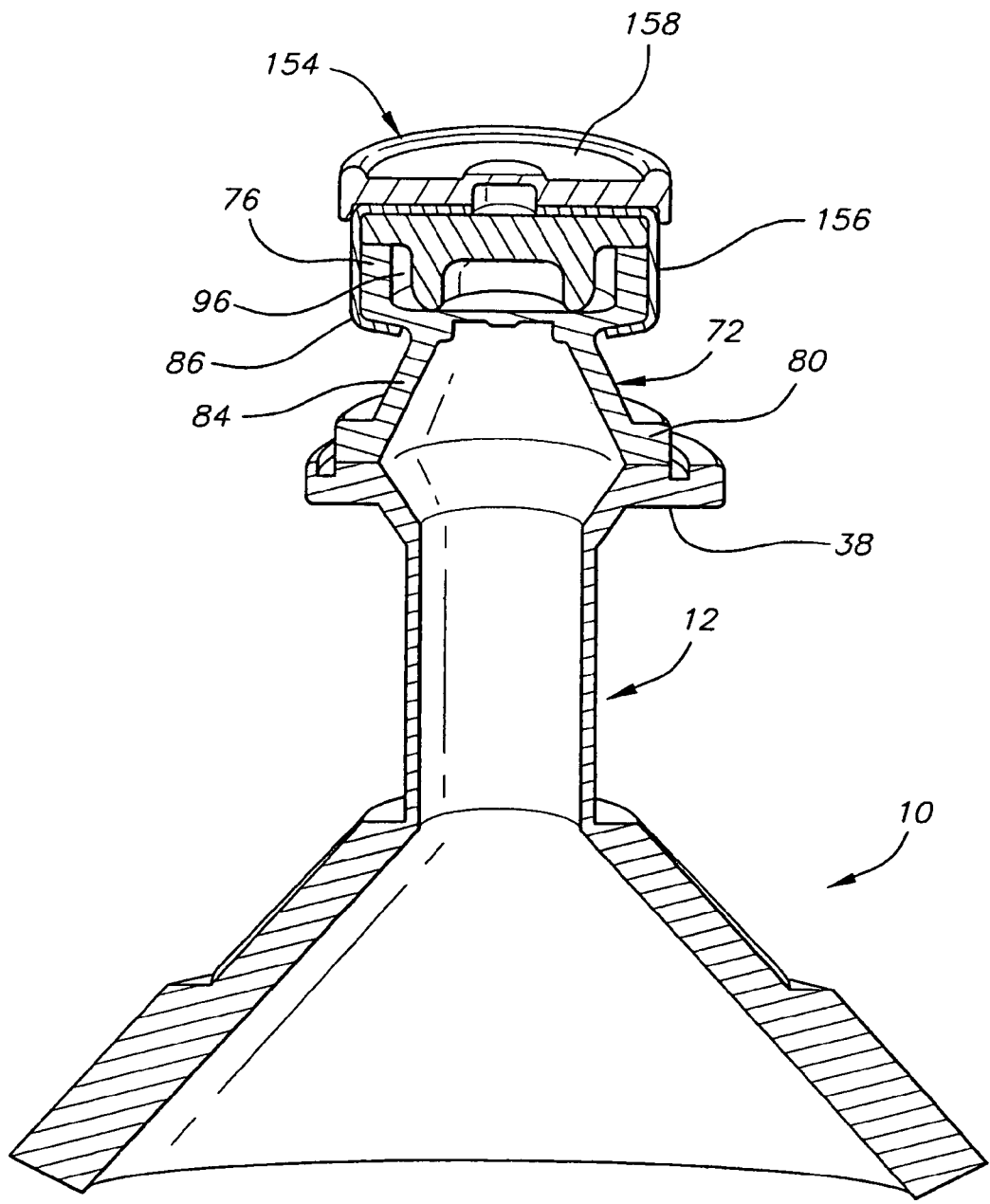
FIG. 16 is a semi-schematic partial perspective cross-sectional side view of the terminal port of FIG. 6 attached to the container port of FIG. 2, which is still yet another exemplary usable port combination with the container of FIG. 1 provided in accordance with aspects of the present invention.

At the base 102 of the interior tapered portion 104, a reduced diameter section 106 is incorporated to delimit or define the effective area of the central puncture-able seal 92. Hence, the area of central puncture-able seal 92 may increase or decrease depending on the area of the reduced diameter section 106 implemented. In one exemplary embodiment, the diameter of the reduced diameter section 106 is about 5 mm. The interior tapered portion 104 comprises a draft angle of about 5 to about 35 degrees from vertical. As previously discussed, the diameter of the port and the length of the port are preferably selected first and the tapered angle is derived as a dependent variable of the former. By way of example, the diameter at the second end 78 (FIG. 6) is selected to align with the flange 38 of the container port 12. The diameter at the reduced end 74 creates a shoulder for the aluminum shell (FIG. 16). The length of the tapered section is selected for automation purposes.

Figure 9:
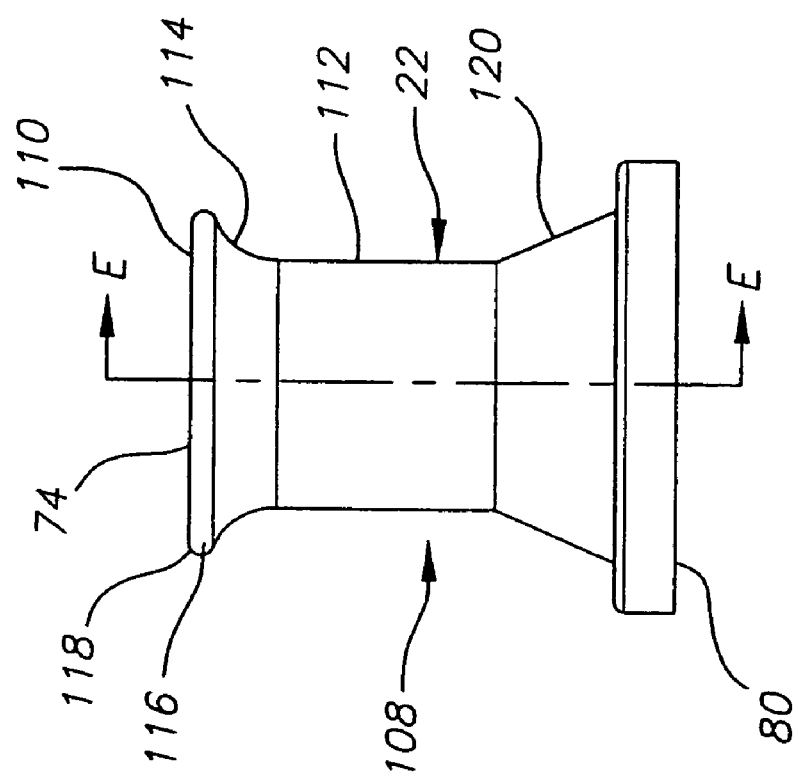
FIG. 9 is a semi-schematic side view of an alternative terminal port usable with the container port of FIG. 2 provided in accordance with aspects of the present invention.

FIG. 9 is a side view of an alternative terminal port 22 provided in accordance with aspects of the present invention, which may specifically be referred to as an additive port 108. The additive port 108 is configured for use with a rubber septum, such as a sleeve stopper made from West Pharmaceutical Services having part number WS-191. The additive port 108 includes a first end 74 comprising a first gripping flange 110 for gripping the sleeve stopper and a second end 78 comprising a mating flange 80 for mating with the flange 38 of the container port 12. In one exemplary embodiment, the gripping flange 110 of the additive port 108 comprises a mid section 112 and the gripping flange 110 flares outwardly from the mid section. The flared section 114 of the gripping flange 110 comprises a curved section comprising a curved radius of about 2.5 mm, a vertical section 116, and an upper curved rim 118 comprising a curved radius of about 0.5 mm with variations thereof being acceptable.

The mating flange 80 extends from a flared section 120. At the interface between the mid section 112 and the flared section 120, the diameter is about 7.62 mm and at the interface between the flared section 120 and the flange, the diameter is about 11.5 mm. The length of the flared section 120 is about 4.41 mm and the mating flange 80 has a flange thickness of about 2 mm. The overall height of the additive port 108 is about 15 mm. The additive port 108 comprises the same material composition as the container port 12 with variations within the range previously disclosed being acceptable. In one exemplary embodiment, the additive port 108 comprises a higher durometer or hardness than the container port 12 for handling purposes during fabricating and filling of the container. Although the additive port 108 is shown with the particular mid section 112, flared section 120, and placement of the puncture-able seal 92 at the intersection of the mid section and the flared section, the additive port may incorporate other configurations. By way of example, the tapered or flared section 120 may have a steeper angle or a more shallow angle, the puncture-able seal 92 may be placed approximately on the same plane as the flange 80, and the mid section may extend towards the length of the port 108 between the flange 80 and the gripping flange 110 without the tapered section 120.

Figure 10:
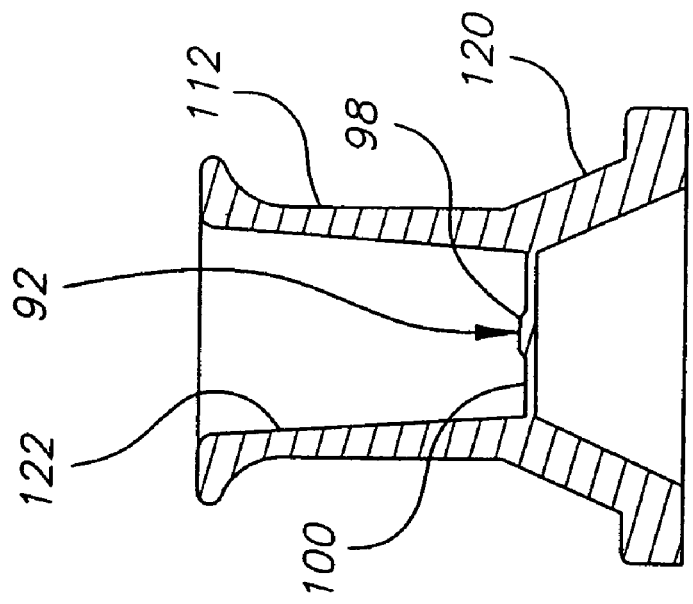
FIG. 10 is a semi-schematic cross-sectional side view of the port of FIG. 9 taken along line E-E.

FIG. 10 is a cross-sectional side view of the additive port 108 of FIG. 9. Similar to the port of FIG. 8, the additive port 108 comprises a central puncture-able seal 92 comprising a raised central portion 98 and a shallow perimeter portion 100. The central puncture-able seal 92 is positioned approximately near the transition between the mid section 112 and the tapered section 120 with the particular placement being dependent on the particular sleeve stopper selected.

To facilitate insertion of the sleeve stopper, a tapered interior cavity comprising a tapered wall 122 is incorporated. However, depending on the configuration of the sleeve stopper, the interior cavity may comprise a straight interior cavity or other corresponding configuration.

Figure 11:
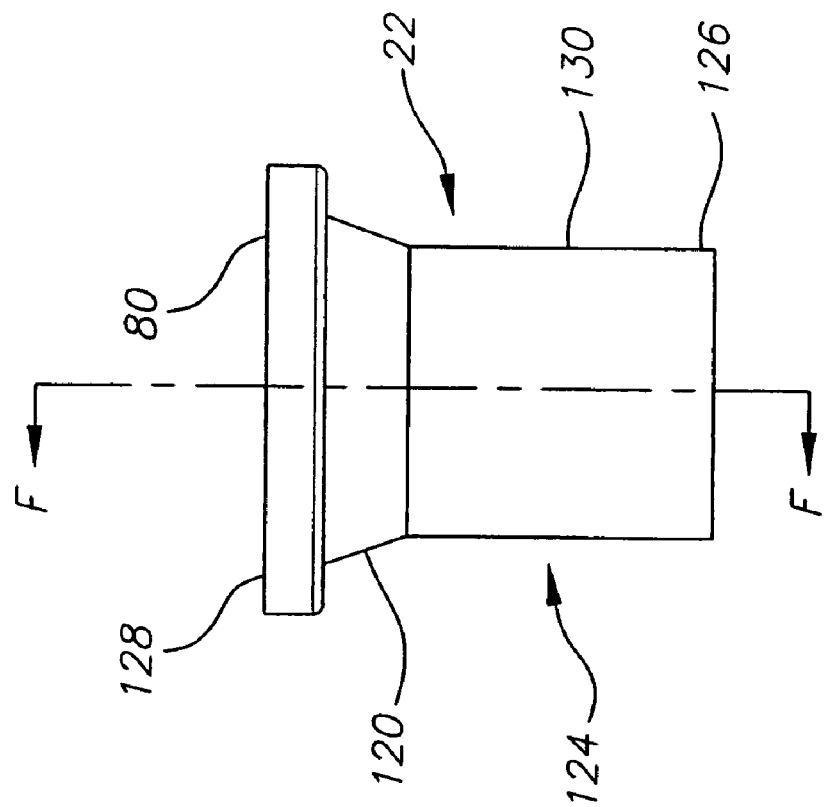
FIG. 11 is a semi-schematic side view of an alternative terminal port usable with the container port of FIG. 2 provided in accordance with aspects of the present invention.

FIG. 11 is a semi-schematic side view of an alternative terminal port 22 provided in accordance with aspects of the present invention, which may be referred to as a set port or an infusion set port 124. The set port 124 comprises a first end 126 comprising a square finish and a second end 128 comprising a mating flange 80. In between the first end 126 and the second end 128, the set port 124 comprises a generally cylindrical section 130 and a tapered section 120. The location of the interface between the cylindrical section 130 and the tapered section 120 generally corresponds to the requirement for accommodating an infusion set closure piercing device in accordance with 6.4 of ISO 8536-4 standard IV spike for an IV administration set. In one exemplary embodiment, the overall length of the fill port 124 is about 15 mm, the length of the generally cylindrical section 130 is about 10 mm, and the outside diameter of the generally cylindrical section is about 9.0 mm. For manufacturing purposes, the generally cylindrical section 130 may comprise a draft angle of about 1-5 degrees.

Figure 12:
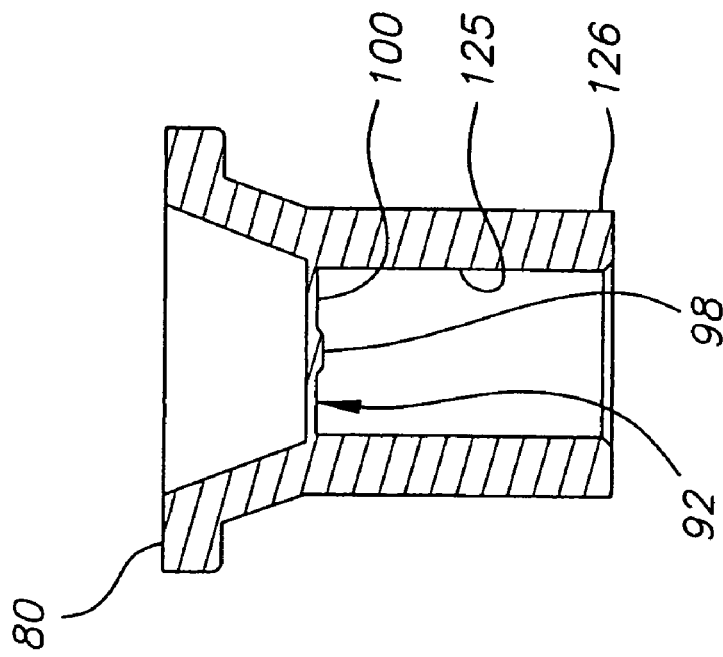
FIG. 12 is a semi-schematic cross-sectional side view of the port of FIG. 11 taken along line F-F.

A cross-sectional side view of the port 124 of FIG. 11 is shown in FIG. 12 taken along line F-F. As shown, a central puncture-able seal 92 is incorporated, which comprises a raised central portion 98 and a shallow perimeter portion 100. As readily apparent, the central puncture-able seal 92 may instead be incorporated without the raised central portion 98. The inside diameter of the set port 124 and the placement of the central puncture-able seal 92 relative to the length of the port may be dependent on the particular chosen IV spike set to be used with the set port. In an alternative embodiment, a puncture-able seal 92 without the protruding or raised central portion 98 may be incorporated or still alternatively, the raised central portion 98 may extend towards the second end 118, on the end with the mating flange 80. Still alternatively, the interior surface 125 of the set port 124 may include a contour or an undulating surface for improve gripping of a spike or an IV administration set or for receiving a rubber septum.

The set port 124 may be useable with the container 10 of FIG. 1 by attaching the set port to either the first container port 12 or the second container port 14. The set port is preferably attachable to the first 12 or second 14 port by heat sealing the mating flange 80 with the flange 38 of the first or second port. For maintaining sterility, the first end 126 is preferably sealed. In one exemplary embodiment, the first end may be sealed with an innerseal. Exemplary innerseals and methods for using the same include foil innerseals disclosed in U.S. Pat. Nos. 5,702,015; 5,860,544, 5,915,577; and 6,461,714, assigned to Selig Sealing Products, Inc., of Oakbrook Terrace, Ill., and their equivalents. The contents of these patents are incorporated herein by reference. Other innerseals may include a laminated aluminum foil material heat bonded to the end of the first end 126 through conventional means.

Figure 13:
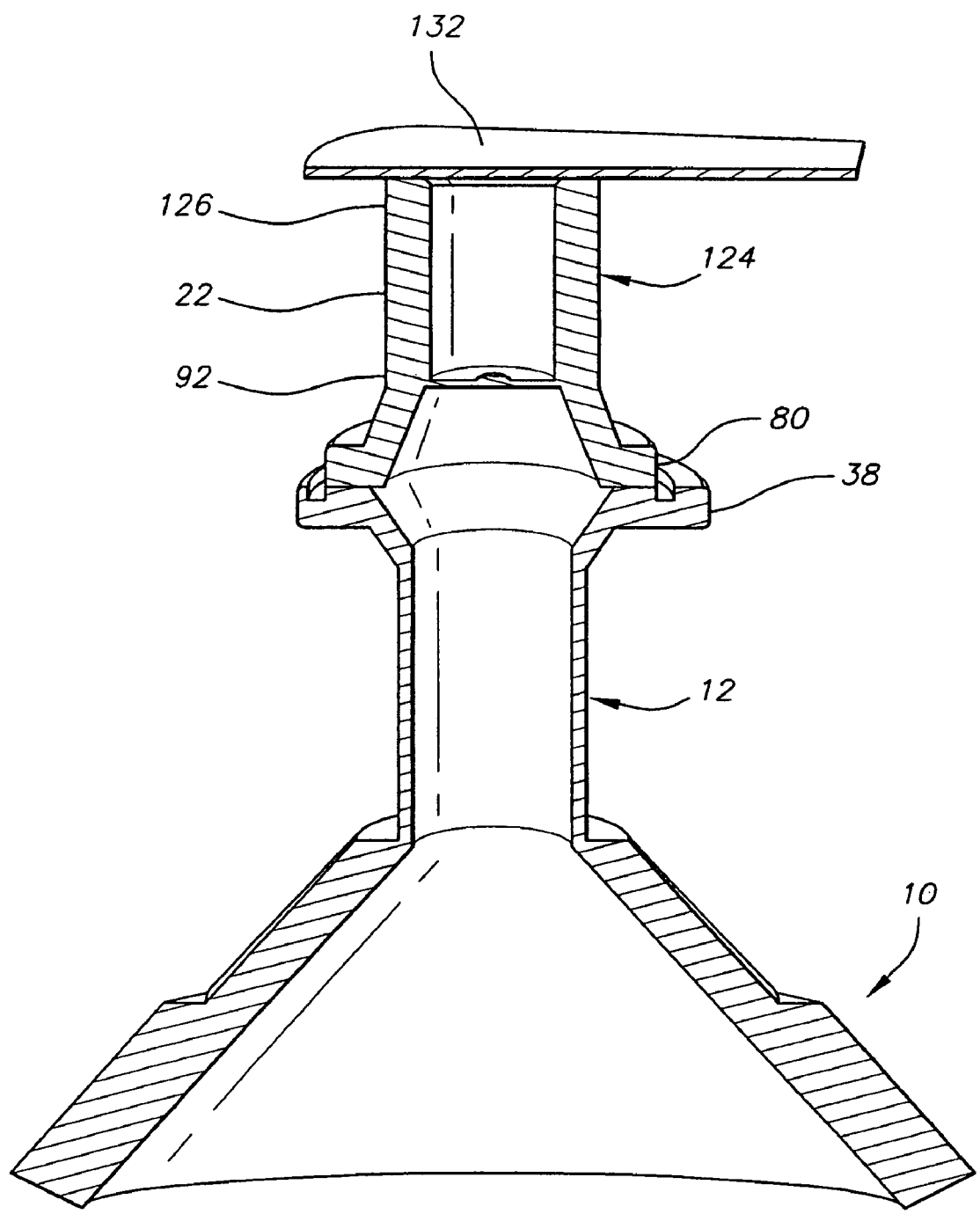
FIG. 13 is a semi-schematic partial perspective cross-sectional side view of the terminal port of FIG. 11 attached to the container port of FIG. 2, which is an exemplary usable port combination with the container of FIG. 1 provided in accordance with aspects of the present invention.

Referring now to FIG. 13, a partial perspective cross-sectional side view of the set port 124 of FIG. 11 is shown attached to the port 12 of FIG. 1. For clarity purposes, the container port 12 is shown without the first 16 and second 18 sheets. The mating flange 80 of the set port 124 is shown heat sealed to the flange 38 of the container port 12 by a radiant heat or hot bar sealing process. The heat sealing step is preferably performed subsequent to the container 10 being filled via the port 12 with, for example, amino acid solution or dextrose solution.

An innerseal 132 is attached to the end of the first end 126 of the set port 124 by conventional means. To excess the contents of the container 10, the innerseal 132 is peeled off of the set port 124 and a spike connector (not shown) is inserted, which then punctures the central puncture-able seal 92 to provide fluid communication between the container and the IV administration set (not shown).

Figure 14:
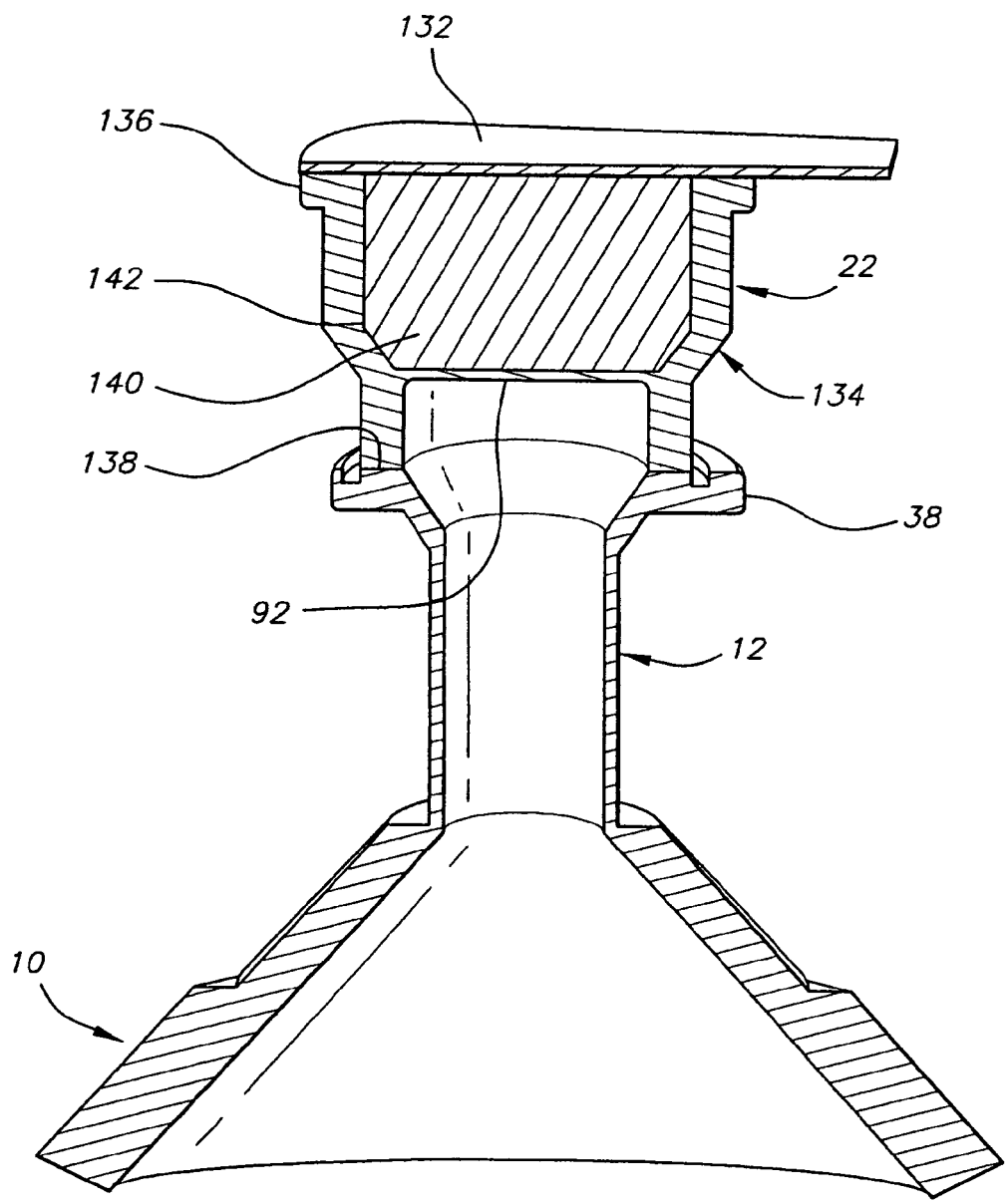
FIG. 14 is a semi-schematic partial perspective cross-sectional side view of an alternative terminal port attached to the container port of FIG. 2, which is another exemplary usable port combination with the container of FIG. 1 provided in accordance with aspects of the present invention.

FIG. 14 is a partial perspective cross-sectional side view of an alternative terminal port 22 provided in accordance with aspects of the present invention. The terminal port 22 may be referred to as a dripless set port 134 and shares certain characteristics with the set ports previously discussed. The dripless set port 134 comprises an end comprising a flange 136 and an end comprising a square finish 138, which may incorporate a tapered rim or a tapered edge on both the inside and outside edges. In one exemplary embodiment, the end with the square finish is attached to the flange 38 of the container port 12 and the end comprising the flange 136 is sealed with an innerseal 132. The attachment may be performed by a conventional radiant heat sealing process or equivalent processes.

In another exemplary embodiment, a rubber septum 140 is positioned in the upper cavity 142 of the dripless set port 134 for resealing the port after a needle or a spike connector punctures the septum 140 and the central puncture-able seal 92 and is thereafter removed. The rubber septum may be separately molded and then placed in the upper cavity of the dripless port 134 or may be injection molded directly into the upper cavity. If placed in the upper cavity, the rubber septum may simply seat in the upper cavity 142 of the port and held there by the compression supplied by an interference fit with the interior surface of the upper cavity. In one exemplary embodiment, the rubber septum 140 is also bonded to the upper cavity 142 to ensure that it does dislodge from the upper cavity. In another alternative embodiment, the rubber septum is insert molded with the port and the septum material bonded to the wall of the port.

Figure 15:
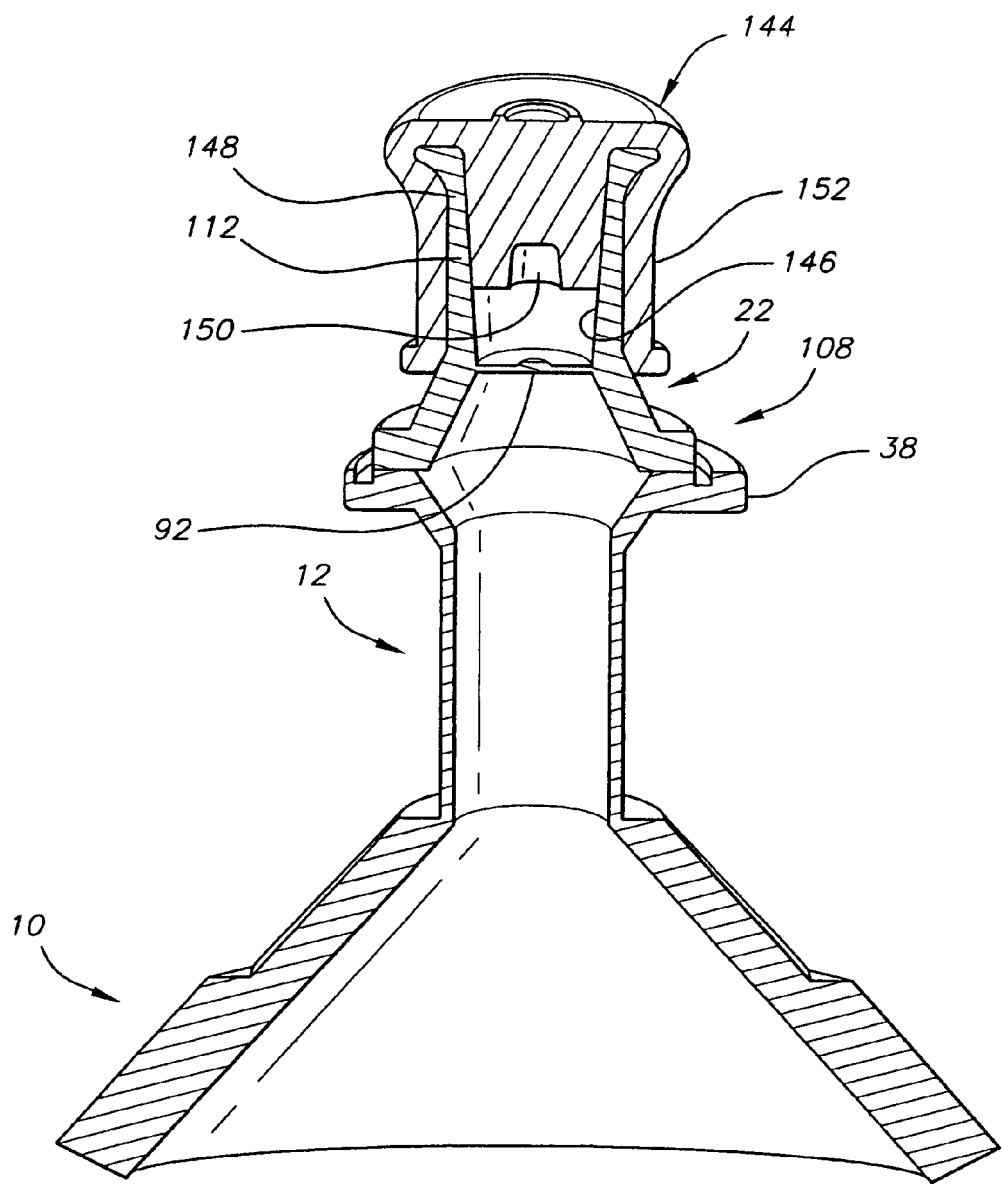
FIG. 15 is a semi-schematic partial perspective cross-sectional side view of the terminal port of FIG. 9 attached to the container port of FIG. 2, which is another exemplary usable port combination with the container of FIG. 1 provided in accordance with aspects of the present invention.

FIG. 15 is a semi-schematic partial perspective cross-sectional side view of the container 10 with the container port 12 attached to the additive port 108 of FIG. 9. The additive port 108 may be bonded to the flange 38 of the container port 12 by conventional means. Either subsequent to but more preferably prior to attaching the additive port 108 to the container port 12, a sleeve stopper 144, which is a rubber septum made by the West Co., is attached to the upper cavity 146 of the additive port The sleeve stopper 144 comprises a male plug 148, a central cut-out 150 in the male plug end to define the septum thickness for a needle to penetrate with reasonable force, and a pliable skirt section 152. The pliable skirt section 152 normally extends away from the male plug 148 prior to positioning the sleeve stopper 144 over the additive port 108. Subsequent to inserting the male plug 148 into the upper cavity 146 of the additive port 108, the skirt 152 is folded over so that the skirt overlaps at least a portion of the exterior mid section 112 of the port 108. In one exemplary embodiment, the male plug 148 and the upper cavity 146 of the additive port comprise complementary tapered sections.

FIG. 16 is a semi-schematic partial perspective cross-sectional side view of the container 10 with the container port 12 attached to the additive port 72 of FIG. 6. In particular, the mating flange 80 of the additive port 72 is attached to the flange 38 of the container port 12 by known radiant heat sealing process. A 13 mm Flip-Off® seal 154 made by the West Co. is then sealed to the receiving chamber 96 by known methods, which includes crimping the aluminum outer shell 156 to the exterior surface of the port at the intersection 86 between the generally cylindrical section 76 and the tapered section 84. Just prior to using the additive port 72 to add supplement drugs or medications into the container, the plastic cap 158 is flipped off by severing a frangible section of the aluminum outer shell 156 to which the cap is attached.

Figure 17:
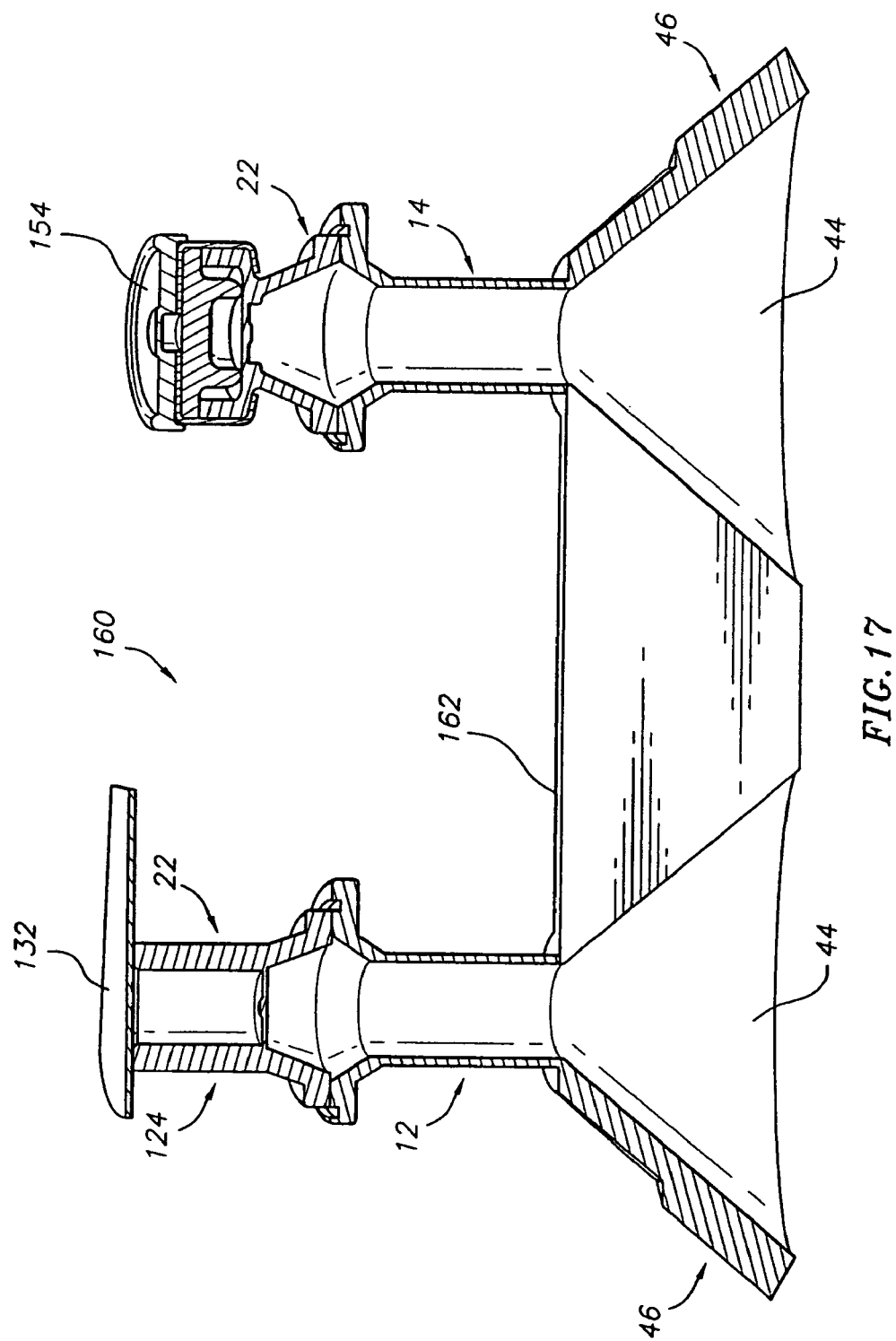
FIG. 17 is a semi-schematic partial perspective cross-sectional side view of a dual port assembly attached to two terminal ports provided in accordance with aspects of the present invention.

Referring now to FIG. 17, a semi-schematic partial perspective cross-sectional view of a dual port assembly 160 provided in accordance with aspects of the present invention is shown. In one exemplary embodiment, the dual port assembly 160 comprises two container ports interconnected by a web 162. The container ports may comprise the container ports 12, 14 shown in FIG. 2 and the web may be an extension of the fins or ribs 46 such that the fins of one port 12 extend to connect with the fins of the other port 14.

The dual port assembly 160 allows two container ports 12, 14 to be assembled between a first sheet 16 and a second sheet 18 to provide means for fluid communication for the flexible container 10 via a single heat sealing step. For example, the attachment flanges 44 of each of the ports may be placed in between the first and second sheets and then by using one or more flat heat dies, fusing the inner surface of the front sheet and the rear sheet to the exterior surface of the attachment flanges 44. The fusion is accomplished by partially melting the surfaces and allowing the melted surfaces to fuse together.

Although the first container port 12 is shown with the set port 124 of FIG. 11 and the second container port 14 is shown with the additive port 72 of FIG. 6, the particular terminal ports 22 are exemplary only. Indeed, any of the terminal ports 22 and associated terminal caps, rubber septums, and/or innerseals discussed above and their equivalents may be used with the present dual port assembly 160.

As readily apparent, in a container 10 comprising two or more container ports 12, 14, the terminal ports 22 may be attached to the two or more container ports before the container is filled with fluids with the exception of at least one container port, which should be left open until after the container is filled. However, it is also possible to attach the terminal ports 22 for all of the container ports after the container is filled.

Figure 18:
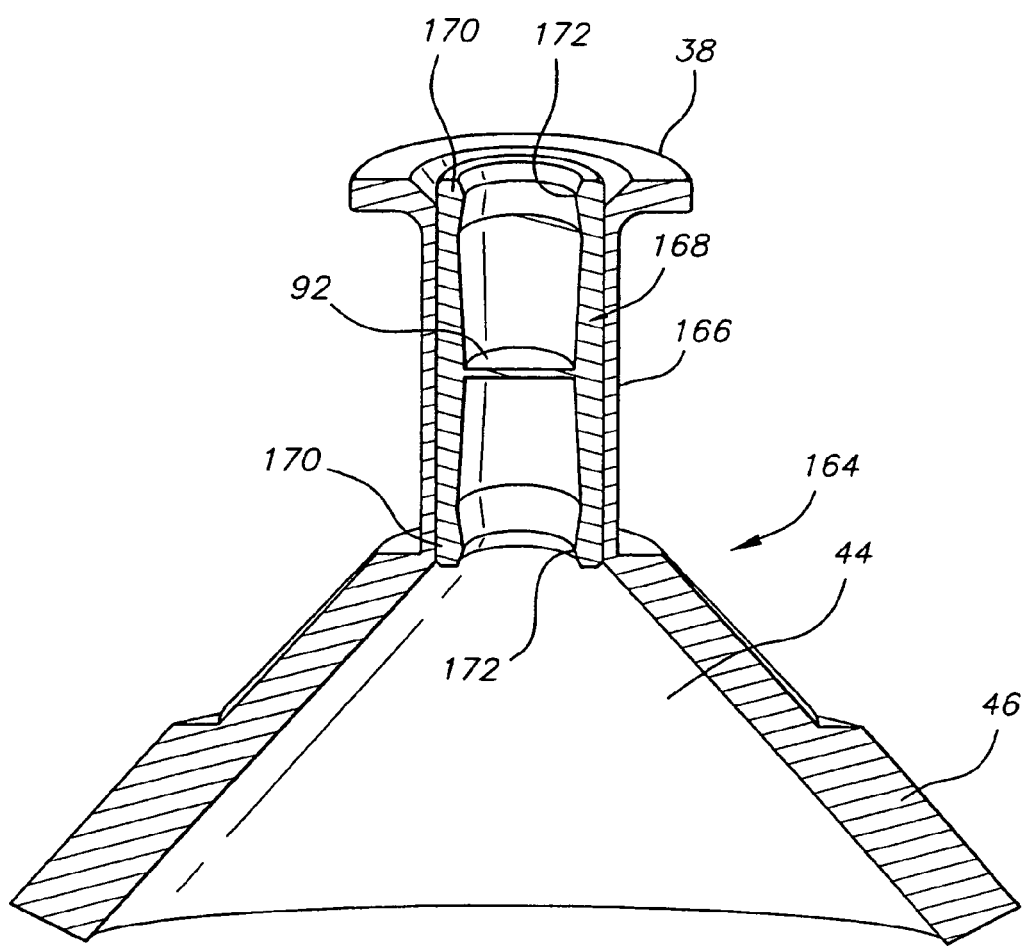
FIG. 18 is a semi-schematic partial perspective cross-sectional side view of an alternative combination container port provided in accordance with aspects of the present invention.

Referring now to FIG. 18, a semi-schematic partial perspective cross-sectional view of a modified container port 164 provided in accordance with aspects of the present invention is shown. The container port 164 is similar to the container port 12 of FIG. 2 in that it comprises a flexible attachment flange 44, fins 46, a nozzle 166, and a flange 38.

The nozzle 166 in the present modified container port 164 is adapted to accept a seal sleeve 168, which may slide into the cavity of the container port 164 and bonded or permanently heat welded in place with conventional methods, such as by a radiant heat sealing process. The seal sleeve may also be retained by mechanical interference with the nozzle. The seal sleeve 168 comprises a generally cylindrical section with a central puncture-able seal 92 disposed in between its two ends 170. The central puncture-able seal 92 is integrally molded to the seal sleeve 168 and, in one embodiment, is disposed at about the mid-way point between the two ends. The seal sleeve is symmetric to facilitate assembly. When the seal sleeve 168 is permanently attached to the container port 164, the container port 164 transforms into a set or drain port useable with a standard spike assembly. Accordingly, the seal sleeve 168, the nozzle, and the flange 38 are dimensioned to accept or accommodate a standard spike assembly.

One or two reduced diameter sections 172 at each end of the seal sleeve 168 may be incorporated to facilitate gripping the spike assembly (not shown) as the spike assembly is inserted into the port 164. The reduced diameter sections 172 are configured to grip a portion of the spike assembly to prevent the same from dislodging therefrom. For sterility, an innerseal may be sealed to the flange 38 of the container port 164. Alternatively, a terminal cover or a cap may be attached to the port.

Although the preferred embodiments of the invention have been described with some specificity, the description and drawings set forth herein are not intended to be delimiting, and persons of ordinary skill in the art will understand that various modifications may be made to the embodiments discussed herein without departing from the scope of the invention, and all such changes and modifications are intended to be encompassed within the appended claims. Various changes to the container comprising one or more flat ports comprising flexible attachment flanges for heat sealing the same to the front and rear sheets of the container with flat heat bars may be made without deviating from the spirit and scope of the present invention. For example, the dimensions of the ports and container can vary, the percent material compositions can vary, and the materials can vary. Other changes include using different terminal ports for different rubber septums, mixing or adding colors and labeling to the components of the container, adding ports to multiple edges of the container along with peelable seals to form a container comprising multiple compartments, and using different bonding means to join the various container ports, terminal ports, and terminal caps together. Accordingly, many alterations and modifications may be made by those comprising ordinary skill in the art without deviating from the spirit and scope of the invention.

What is claimed is:

1. A flexible container comprising:
   a flexible front sheet and a flexible rear sheet attached to one another along at least a portion of a common perimeter to define an interior cavity;
   a container port comprising a nozzle attached to a flexible attachment flange, which is attached to the flexible front and rear sheets;
      wherein the flexible flange comprises a first flange layer comprising an interior surface and an exterior surface attached to a second flange layer comprising an interior surface and an exterior surface; the two flange layers defining an interior cavity comprising a first opening near the nozzle and a larger second opening near the flexible front and rear sheets; and
      wherein the attachment flange is pliable such that at least a portion of the interior surface of the first flange layer contacts at least a portion of the interior surface of the second flange layer when the flexible attachment flange is compressed between the flexible front sheet and flexible rear sheet.

2. The flexible container of claim 1, wherein the first and second flange layers are connected together along two common edges.

3. The flexible container of claim 2, wherein the two common edges are creases formed from integrally molding the first and second flange layers.

4. The flexible container of claim 2, wherein the two common edges each comprises a fin.

5. The flexible container of claim 4, wherein the fins extend outwardly from the two common edges.

6. The flexible container of claim 5, wherein the fins each tapers as it extends outwardly away from the common edge that it extends from.

7. The flexible container of claim 1, wherein the flexible front and rear sheets each comprises a multi-layer film.

8. The flexible container of claim 7, wherein the multi-layer film comprises three distinct film layers.

9. The flexible container of claim 7, wherein a layer of the multi-layer film is made from a blend of polypropylene-ethylene random copolymer and styrene ethylene-butylene styrene (SEBS) thermoplastic elastomer.

10. The flexible container of claim 9, wherein a second layer of the multi-layer film is made from either a polyether block amide copolymer (PEBA) or an abuse resistant material containing ester groups (EGM).

11. The flexible container of claim 10, wherein a third layer of the multi-layer film is made from SEBS if the second layer is made from EGM, and wherein the third layer is made from carboxy modified polypropylenes if the second layer made from PEBA.

12. The flexible container of claim 1, wherein the container port is made from a blend of polypropylene-ethylene random copolymer and styrene ethylene-butylene styrene thermoplastic elastomer.

13. The flexible container of claim 12, wherein the blend is in a weight-weight ratio of about 90:10 to about 70:30 of polypropylene-ethylene random copolymer to styrene ethylene-butylene styrene.

14. The flexible container of claim 1, further comprising a powder medicament, a liquid medicament, or both in the interior cavity.

15. A method for forming a flexible container comprising:
   joining a flexible front sheet to a flexible rear sheet along at least a portion of a common perimeter to define an interior cavity;
   placing a flexible attachment flange in between the flexible front sheet and flexible rear sheet, said attachment flange having a container port comprising a nozzle attached thereto;
      wherein the flexible attachment flange comprises a first flange layer, which has an exterior surface and an interior surface, attached to a second flange layer, which has an exterior surface and an interior surface;

applying a heat bar over at least one of the flexible front sheet and the flexible rear sheet to compress the attachment so that the interior surface of the first flange layer collapses towards the interior surface of the second flange layer to seal the attachment flange to the flexible front and rear sheets.

16. The method of claim 15, further comprising attaching a second attachment flange, which has a port attached thereto, to the flexible front and rear sheets.

17. The method of claim 15, wherein the attachment flange has two tapered edges.

18. The method of claim 15, further comprising adding a powder medicament, a liquid medicament or both to the interior cavity.

19. The method of claim 15, further comprising joining the flexible front sheet with the flexible rear sheet by a peelable seal to create a compartment.

20. The method of claim 15, wherein the nozzle is attached to a terminal port.

21. The method of claim 20, further comprising a peelable foil layer attached to the terminal port.

22. The method of claim 21, wherein the flexible front sheet or the rear sheet or both comprise a multi-layer film.

23. A method for forming a flexible container comprising:
joining a flexible front sheet to a flexible rear sheet along at least a portion of a common perimeter to define a cavity;
placing a flexible attachment flange in between the flexible front sheet and the flexible rear sheet in a weld area for attaching the attachment flange to the flexible front and rear sheets, the flexible attachment flange comprising a first flange layer and a second flange layer and a container port;
applying at least one heat bar to the weld area to attach the attachment flange to the flexible front and rear sheets, said heat bar causing the first flange layer to collapse towards the second flange layer during the applying step.

24. The method of claim 23, wherein the flexible front sheet or the flexible rear sheet or both comprise a multi-layer film.

25. The method of claim 24, wherein the multi-layer film comprises three distinct film layers.

26. The method of claim 25, wherein a layer of the multi-layer film is made from a blend of polypropylene-ethylene random copolymer and styrene ethylene-butylene styrene (SEBS) thermoplastic elastomer.

27. The method of claim 26, wherein a second layer of the multi-layer film is made from either a polyether block amide copolymer (PEBA) or an abuse resistant material containing ester groups (EGM).

28. The method of claim 27, wherein a third layer of the multi-layer film is made from SEBS if the second layer is made from EGM, and wherein the third layer is made from carboxy modified polypropylenes if the second layer made from PEBA.

29. The method of claim 23, wherein the container port is made from a blend of polypropylene-ethylene random copolymer and styrene ethylene-butylene styrene thermoplastic elastomer.

30. The method of claim 29, wherein the blend is in a weight-weight ratio of about 90:10 to about 70:30 of polypropylene-ethylene random copolymer to styrene ethylene-butylene styrene.

31. The method of claim 23, further comprising a powder medicament, a liquid medicament, or both in the interior cavity.

32. The method of claim 31, wherein the cavity is divided into a first compartment by a peelable seal for containing the liquid medicament and a second compartment for containing the powder medicament.

33. The method of claim 23, wherein the flexible front sheet and the flexible rear sheet are connected to one another along a singularly formed fold line.

* * * * *

UNITED STATES PATENT AND TRADEMARK OFFICE
CERTIFICATE OF CORRECTION

PATENT NO. : 7,618,405 B2
APPLICATION NO. : 12/025282
DATED : November 17, 2009
INVENTOR(S) : Harvey Theodore Young It is certified that error appears in the above-identified patent and that said Letters Patent is hereby corrected as shown below:

In column 6, line 9-10, delete "cyclohexanedimethano" and insert -- cyclohexanedimethanol --, therefor.

In column 12, line 9, after "port" insert -- . --.

In column 14, line 53-54, in Claim 13, delete "ethyl ene-butylene" and insert -- ethylene-butylene --, therefor.

Signed and Sealed this

Thirtieth Day of November, 2010

David J. Kappos
*Director of the United States Patent and Trademark Office*